US007473235B2

(12) United States Patent
Schwenn et al.

(10) Patent No.: US 7,473,235 B2
(45) Date of Patent: Jan. 6, 2009

(54) LIGHTWEIGHT MODULAR ADJUSTABLE PROPHYLACTIC HIP ORTHOSIS

(75) Inventors: Shannon R. Schwenn, Deltona, FL (US); Robert B. Hamilton, III, Orlando, FL (US); John N. Penn, Orlando, FL (US); Michael M. Brady, Mission Viejo, CA (US)

(73) Assignee: Orthomerica Products, Inc., Orlando, FL (US)

( * ) Notice: Subject to any disclaimer, the term of this patent is extended or adjusted under 35 U.S.C. 154(b) by 174 days.

(21) Appl. No.: 11/212,287

(22) Filed: Aug. 26, 2005

(65) Prior Publication Data

US 2005/0283102 A1 Dec. 22, 2005

Related U.S. Application Data

(63) Continuation-in-part of application No. 10/755,515, filed on Jan. 12, 2004, now Pat. No. 7,186,229, which is a continuation of application No. 09/730,362, filed on Dec. 5, 2000, now Pat. No. 6,676,620.

(51) Int. Cl.
*A61F 5/00* (2006.01)
*A61F 5/24* (2006.01)
*A61F 5/28* (2006.01)
*A61F 5/26* (2006.01)

(52) U.S. Cl. .......................... 602/16; 602/19; 128/96.1; 128/99.1; 128/100.1; 128/101.1; 2/311; 2/312; 2/321

(58) Field of Classification Search .................. 602/19, 602/16, 23, 24; 128/96.1, 99.1, 100.1, 101.1; 2/311, 312, 321
See application file for complete search history.

(56) References Cited

U.S. PATENT DOCUMENTS

| | | | |
|---|---|---|---|
| 61,487 | A | 1/1867 | Vollschwitz |
| 181,948 | A | 9/1876 | Kleinschuster |
| 232,420 | A | 9/1880 | Smith |
| 321,145 | A | 6/1885 | Spencer |
| 321,146 | A | 6/1885 | Spencer |
| 328,638 | A | 10/1885 | Battershall |
| 386,642 | A | 7/1888 | Mann |

(Continued)

OTHER PUBLICATIONS

Brochure: Cybertech 2000, Chairback, The Rigid Mechanical Advantage Orthoses, 1998.

(Continued)

*Primary Examiner*—Patricia Bianco
*Assistant Examiner*—Tarla Patel

(57) ABSTRACT

The present invention provides a universally applicable orthosis such as a hip orthosis and includes a semi-rigid hip engaging unit that can be easily bent for attachment to a user's waist. A semi-rigid thigh support member is also easily bent for attachment to either the right or the left thigh of a user. A closure unit enables the user to provide a compressive force on the waist with a mechanical force advantage. The hinge unit extends between the hip engaging unit and the thigh unit to stabilize the limit of the extension and rotation of the thigh relative to the waist of the user. Although the waist engaging unit and the thigh support member are relatively flexible when they bend about the user, they are structured to become rigid to provide stable anchor points for the hinge unit.

11 Claims, 7 Drawing Sheets

U.S. PATENT DOCUMENTS

| | | | | |
|---|---|---|---|---|
| 571,749 | A | 11/1896 | Colton | |
| 601,446 | A | 3/1898 | Mestler | |
| 629,900 | A | 8/1899 | Fosburgh | |
| 746,563 | A | 12/1903 | McMahon | |
| 772,926 | A | 10/1904 | Colton | |
| 787,894 | A | 4/1905 | McMahon | |
| 894,066 | A | 7/1908 | Scarpa | |
| 1,060,422 | A | 4/1913 | Bowdish | |
| 1,393,188 | A | 10/1921 | Whiteman | |
| 1,463,579 | A | 7/1923 | Funck | |
| 1,469,661 | A | 10/1923 | Migita | |
| 1,481,903 | A | 1/1924 | Hart | |
| 1,530,713 | A | 3/1925 | Clark | |
| 1,558,661 | A | 10/1925 | Yeganian | |
| 2,036,484 | A | 4/1936 | Le May | |
| 2,100,964 | A | 11/1937 | Kendrick | |
| 2,117,309 | A | 5/1938 | Fritsch | |
| 2,219,475 | A | 10/1940 | Flaherty | |
| 2,409,381 | A | 10/1946 | Pease, Jr. | |
| 2,554,337 | A | 5/1951 | Lampert | |
| 2,749,550 | A | 6/1956 | Pease | |
| 3,371,351 | A | 3/1968 | Allain | |
| 3,834,048 | A | 9/1974 | Maurer | |
| 3,927,665 | A | 12/1975 | Wax | |
| 4,099,524 | A | 7/1978 | Cueman et al. | |
| 4,175,553 | A | 11/1979 | Rosenber | |
| 4,475,543 | A | 10/1984 | Brooks et al. | |
| 4,508,110 | A | 4/1985 | Modglin | |
| 4,574,789 | A | 3/1986 | Forster | |
| 4,658,807 | A | 4/1987 | Swain | |
| 4,696,291 | A | 9/1987 | Tyo | |
| 4,862,878 | A | 9/1989 | Davison et al. | |
| 4,870,761 | A | 10/1989 | Tracy | |
| 4,905,678 | A * | 3/1990 | Cumins et al. | 602/16 |
| 4,937,952 | A | 7/1990 | Olivieri | |
| 5,072,725 | A | 12/1991 | Miller | |
| 5,074,288 | A | 12/1991 | Miller | |
| 5,226,874 | A | 7/1993 | Heinz et al. | |
| 5,259,831 | A | 11/1993 | LeBron | |
| 5,346,461 | A | 9/1994 | Heinz et al. | |
| 5,399,151 | A | 3/1995 | Smith | |
| 5,437,617 | A | 8/1995 | Heinz et al. | |
| 5,484,395 | A | 1/1996 | DeRoche | |
| 5,499,965 | A | 3/1996 | Sanchez | |
| 5,599,287 | A | 2/1997 | Beczak, Sr. et al. | |
| 5,634,891 | A | 6/1997 | Beczak, Sr. et al. | |
| 5,853,378 | A | 12/1998 | Modglin | |
| 5,857,988 | A | 1/1999 | Shirley | |
| 5,967,998 | A | 10/1999 | Modglin | |
| 6,110,138 | A | 8/2000 | Shirley | |
| 6,190,343 | B1 | 2/2001 | Heinz et al. | |
| 6,213,968 | B1 | 4/2001 | Heinz et al. | |
| 6,322,529 | B1 | 11/2001 | Chung | |
| 6,494,853 | B1 * | 12/2002 | Rossi et al. | 602/16 |
| 6,517,502 | B2 * | 2/2003 | Heyman et al. | 602/5 |
| 6,676,620 | B2 * | 1/2004 | Schwenn et al. | 602/12 |
| 7,186,229 | B2 * | 3/2007 | Schwenn et al. | 602/19 |
| 7,201,727 | B2 * | 4/2007 | Schwenn et al. | 602/12 |
| 2002/0148461 | A1 | 10/2002 | Heinz et al. | |

OTHER PUBLICATIONS

Brochure: Cybertech 2000, Body Jacket, The Rigid Mechanical Advantage Orthoses, 1998.

Brochure: Cybertech 2000, Cruiciform Anterior Spinal Hyperextension, The Rigid Mechanical Advantage Orthoses, 1998.

Brochure: Cybertech 2000, TLSO, The Rigid Mechanical Advantage Orthoses, 1998.

Brochure: Cybertech 500, New LSO, The Mechanical Advantage Orthoses, 1998.

Brochure: Cybertech 1000, The Mechanical Advantage Orthoses, 1998.

Brochure: Orthomerica Products, Inc., Lite Torso Spinal System, 1995.

* cited by examiner 70
68
66
82
88
78
92
92
84
72

10
20
18
50
62

200
10
14
20
52
16
50
18
102
6
99
98
96
94
100
7
101
82
104
64
66
68
62
84
92
78
86
88
90
41
12
11

100
101
108
110
101
108
106
66
64
70
68

102
104
99
40
104
99
98
60
12
65
63
61

102
112

65
58
54
56
60

68
76
74
78
66
80

66
68
72
70

61
63
60

LIGHTWEIGHT MODULAR ADJUSTABLE PROPHYLACTIC HIP ORTHOSIS

RELATED APPLICATIONS

This application is a Continuation-in-Part of Ser. No. 10/755,515 U.S Pat. No. 7,186,229 filed on Jan. 12, 2004 which is a Continuation of Ser. No 09/730,362 U.S. Pat. No. 6,676,620 filed on Dec. 5, 2000.

BACKGROUND OF THE INVENTION

1. Field of the Invention

The present invention is directed to an orthotic brace and more particularly to an orthosis having modular component parts, such as a hip orthosis of a lightweight design that can be easily mounted and tightened on a patient for example as one possible use, to address a post-operative treatment of hip arthoplatyies.

2. Description of Related Art

Orthotic management of hip joint compromise has been a challenge for orthopaedics, orthotists, and therapists when dealing with patients whose hip joints and their associated soft tissues, joint integrity, alignment, and bone and capsular components are compromised. A hip is a multidirectional joint capable of flexion, extension, internal and external rotation, adduction, and abduction. In addition to its mobility, the hip joint must absorb the force of full weight-bearing and provide stability to the pelvis both for standing and for single support during gait. Additionally, during walking, while one hip is stabilized, the opposite leg must have the strength, range of motion, and structural integrity to advance.

The hip joint is a synovial ball and socket joint that consists of the articulation of the spherical head of the femur with the cup-like shape of the acetabulum. An acetabular labrum attaches to the bony rim of the acetabulum and cups around the head of the femur to hold it firmly in place. Various ligaments add strength to the articulation of the hip joint and a large number of muscles act on the hip joint. The gluteus medius is primarily associated with abduction. Anterior fibers assist with flexion and internal rotation. Posterior fibers assist with extension and external rotation. These muscle groups stabilize the pelvis during a single leg support.

Frequently, these muscle groups are compromised when surgical procedures are performed at the hip joint, especially during a hip replacement surgery. A significant problem that occurs when a hip joint has been compromised is dislocation of the hip joint. Thus, the femoral head can be driven out of the acetabulum. The hip is most susceptible to posterior dislocation when it is flexed past 90°, internally rotated and adducted. Examples of this action occur in every day living, such as sitting on a low chair and leaning forward while putting weight on the affected hip joint and internally rotating when coming to a standing position. Thus, common activities of daily living, specifically excessive hip flexion with loaded extremity and internal rotation on the affected side, can cause dislocation. Anterior dislocation also occurs when a hip is externally rotated, abducted, and flexed and if, for example, a knee is subject to a force, such as accidentally hitting an object. The neck of the femur or the greater trochanter levels the femur out of the acetabulum. To avoid these problems, an orthosis must be able to effectively control the limits of extension and rotation in a patient who has experienced an anterior dislocation.

The assignee of the present invention has provided orthoses to control extension and external rotation with a line of "NEWPORT®" hip system products.

See, for example, Team Management of Hip Revision Patients Using a Post-Op Hip Orthosis by Lima et al., Journal of Prosthetics and Orthotics, Vo. 6, No. 1, Winter/1994.

Usually a hip orthosis will include relatively rigid plastic shells of a shape to capture and conform to a side of a patient's hip and leg. Such shells can be heat-molded into a shape which conforms to the contours of the average human hip as shown in U.S. Pat. No. 6,589,195.

Another example of an orthotic hip support can be found in U.S. Pat. No. 5,830,168, while a safety device to assist movement of a person can be found in U.S. Pat. No. 5,361,418. An orthopedic hip and leg abductor is disclosed in U.S. Pat. No. 5,361,418.

As the median age of the population becomes older, there are more occasions for the treatment of hip disorders and there is still a need to improve the function of such orthoses and their component parts in this medical field in an economical manner, while addressing a comfort level for the patient to encourage maximize prolonged usage.

The desire in the medical profession is to encourage an early mobility to the patient after hip surgery and to enable the patient to easily don a hip orthosis, with appropriate compression despite the strength of the patient. Preferably the hip orthosis will provide adequate rigidity to stabilize the hip while permitting a comfortable lightweight structure to encourage prolonged use by the patient.

SUMMARY OF THE INVENTION

The present invention is directed to a lightweight modular orthosis and to improvements in pre-fabricated component parts of the modular system for not only a hip orthosis, but for other broader applications in the orthotic field.

The orthosis includes a pelvic support or hip engaging unit that is formed to conform to the contours of the human hip. The hip engaging unit can include a pair of semi-rigid pelvic support members removably attachable to each other at one end. Each of the pelvic support members conform to a portion of the patient's waist to provide basically an encircling configuration with semi-rigid intermediate or central portions that can be bent to flex with relative ease about the vertical axis of the user's waist for conforming to the user's body and enable higher resistance to bending in a traverse axis to thereby provide appropriate stiffness to an anchor portion for securing a hinge unit connection with a semi-rigid thigh support member to limit movement.

Exterior wedge members can be mounted on a pelvic support member in a corresponding thigh support member to provide adjustable interconnection of a hinged unit. Anchor members can also be appropriately mounted within the pelvic support member and the corresponding thigh support member to provide additional rigidity and threaded holes for receiving appropriate fasteners for interconnecting the hinge units with their extension members.

As can be appreciated, the combination of the pelvic support members and compound closure unit can be uniquely utilized also as a modular orthosis apart from a hip orthosis since it provides a relatively lightweight and easily conformable waist support from which an anchor with stabilizing appendage supports to other portions of the body such as an arm or shoulder, can be provided. Thus, the orthosis with a first and second body member having semi-rigid pelvic support can be removably attached to each other while supporting a unique closure unit capable of providing a mechanical force advantage.

Each of a first body member and a second body member can have a semi-rigid panel mounted within a central portion to provide a bending flex about a vertical axis of the user's waist to permit conformity to the user's body for providing a higher resistance to bending in a traverse axis. An anchor member can be mounted on at least one of the first body member and the second body member to support the appendage attachment. In the case of the hip orthosis, a semi-rigid thigh support member can be removably mounted on a thigh of the user and a hinge unit can be appropriately connected between the thigh support member and its corresponding pelvic support member.

A semi-rigid panel can have an approximately trapezoidal shape and can be spaced along the appropriate body member to provide sufficient anchor support while maintaining both a lightweight and flexible configuration.

Preferably exterior coverings of the first body member and second body member utilize a fabric that is relatively breathable and appropriate resilient pads can be arranged within the body members to provide comfort to the patient for maintaining the adequate compression for support.

Each of the first body member and second body member are flexible at their respective ends and can have a nap and hook material to permit a removable attachment by the user. A semi-rigid central portion of the respective body members maintain both the integrity and compressive force advantages of the orthosis while also establishing an anchor point for attachment of appropriate extensions to appendage members. An intermediate flexible portion spaced from the attachment of the connector members that form the closure unit at the distal end of the body members further assists in the flexibility of the body member. The closure unit itself can utilize posts extending radially out from a vertical axis of the user's waist and the parts are interconnected with an elongated member such as a nylon cord so that when the user pulls the nylon cord the displacement of the cord between the posts magnifies the compressive force to provide a mechanical force advantage.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
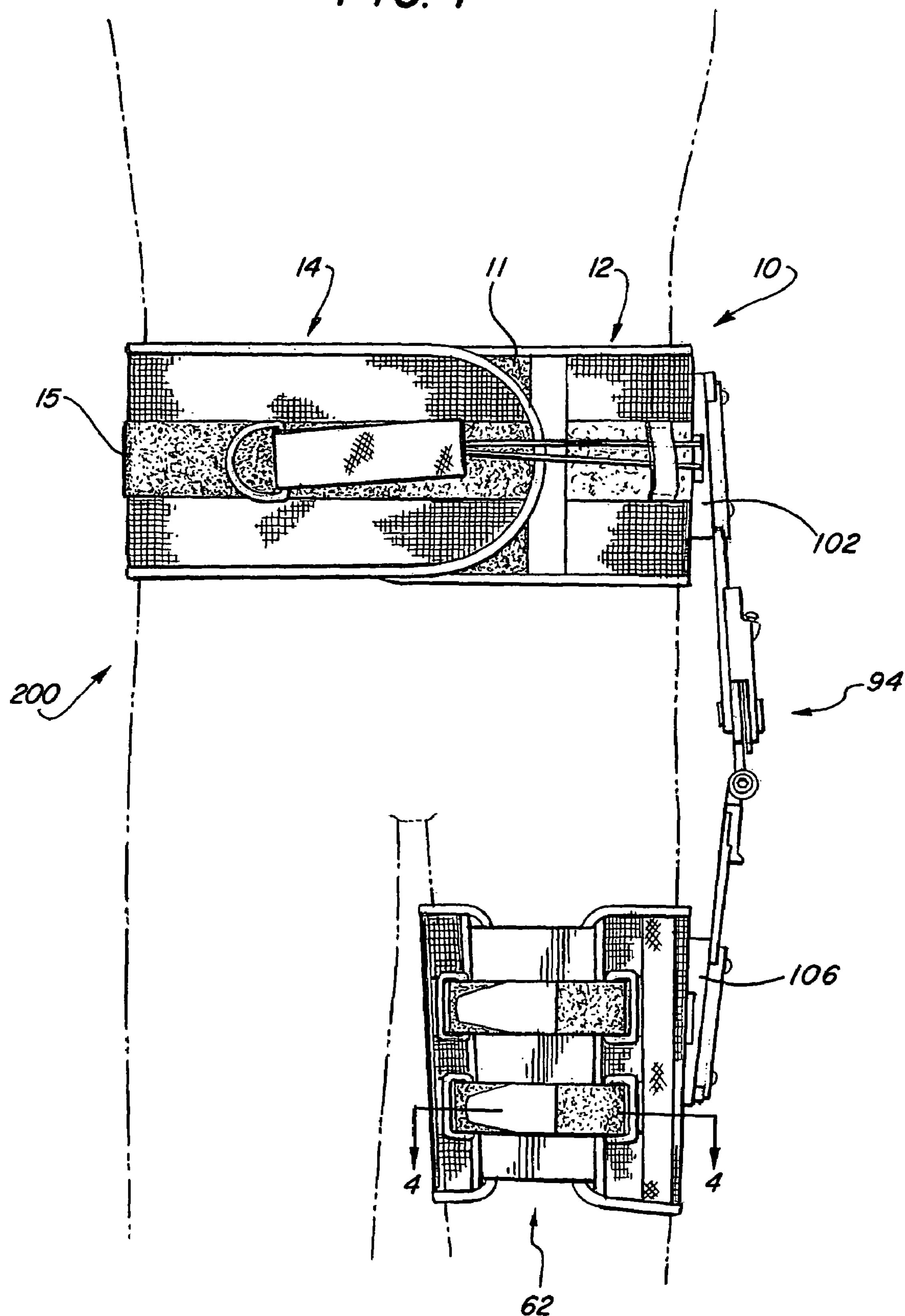
FIG. 1 is a front elevated view of the modular component parts formed in a first embodiment of a hip orthosis of the present invention.

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims.

Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

The following description is provided to enable any person skilled in the orthotic art to make and use the invention. Various modifications, however, will remain readily apparent to those skilled in the art, since the general principles of the present invention have been defined herein specifically to provide an improved modular component orthosis which can be combined together to form an adjustable prophylactic hip orthosis and adduction/abduction joint.

The modular components of the present invention can be combined together to provide an orthosis that can be prefabricated and subsequently adjusted to meet the specific needs and sizes of various patients. Thus, the cost of customized orthoses can be avoided while retaining the advantages of a customized fitting to meet the specific needs of the patient. The utilization of the various modular components can be advantageously incorporated in different types of orthotic applications, since they represent improvements in design and function. Collectively, the modular components can advantageously provide an improved orthosis.

A particular example of such an orthosis is an adjustable prophylactic hip orthosis and abduction joint. While the present invention is described in this environment, it should be readily appreciated that the metes and bounds of this invention are not so limited, since one or more of the modular components can be advantageously utilized in other orthotic applications. For example, the hip engaging unit of the present invention can be utilized to provide a stable platform for supporting orthoses treating shoulder and arm appendages. Likewise, it can provide a stable platform for other orthoses, such as an orthopaedic leg abductor for resisting muscular contraction of the type disclosed in U.S. Pat. No. 5,814,001 and incorporated herein.

Another example of an orthosis that can utilize component parts of the present invention, such as the hip engaging unit, the adjustable support plate, and the connector plate, can be seen in orthopaedic shoulder braces having adjustable pelvic and arm supports shown, for example, in U.S. Pat. Nos. 5,538,499 and 5,487,724 which are incorporated herein by reference.

Referring to FIG. 1, an embodiment of the present invention is disclosed as an adjustable hip orthosis 200. The adjustable hip orthosis 200 is created from pre-fabricated modular component parts that can be custom-adjusted to match motions permitted for a particular patient or user, including flexion, extension, adduction and abduction.

Figure 2:
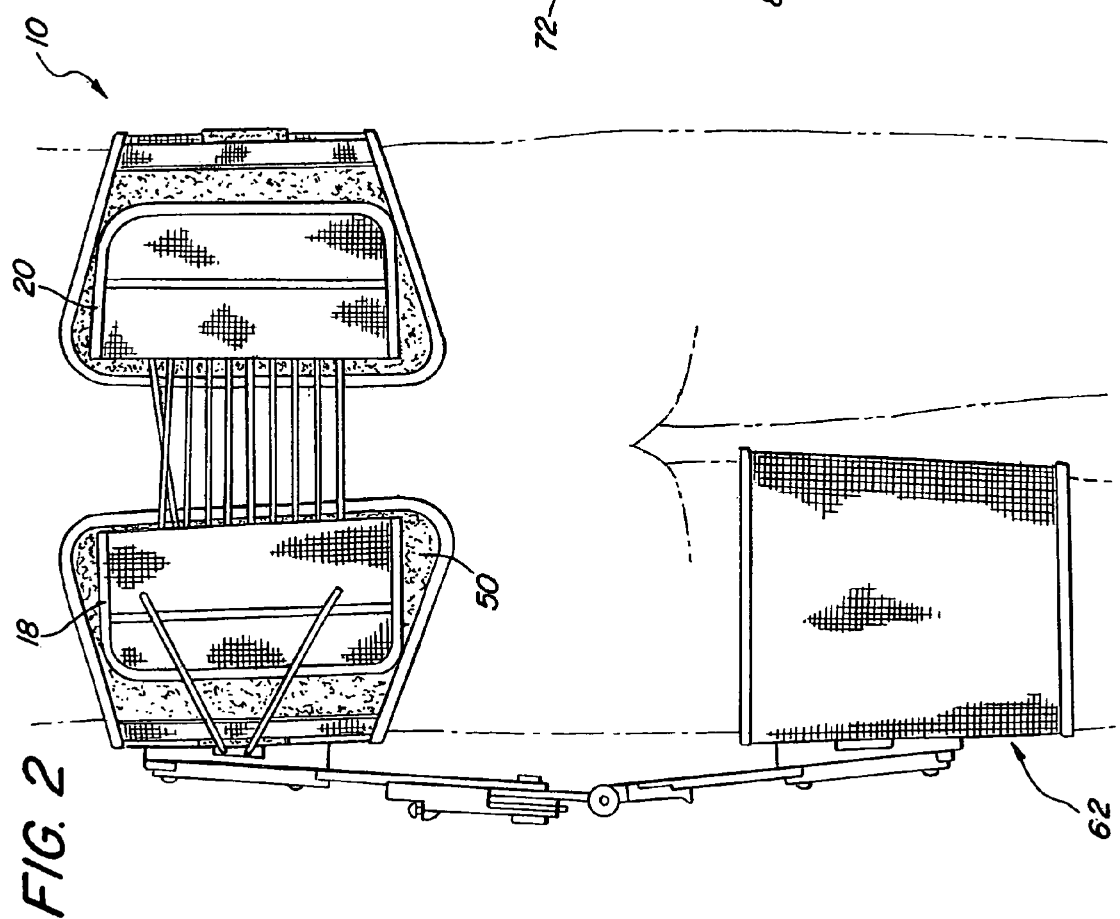
FIG. 2 is a rear elevated view of the hip orthosis.
Figure 3:
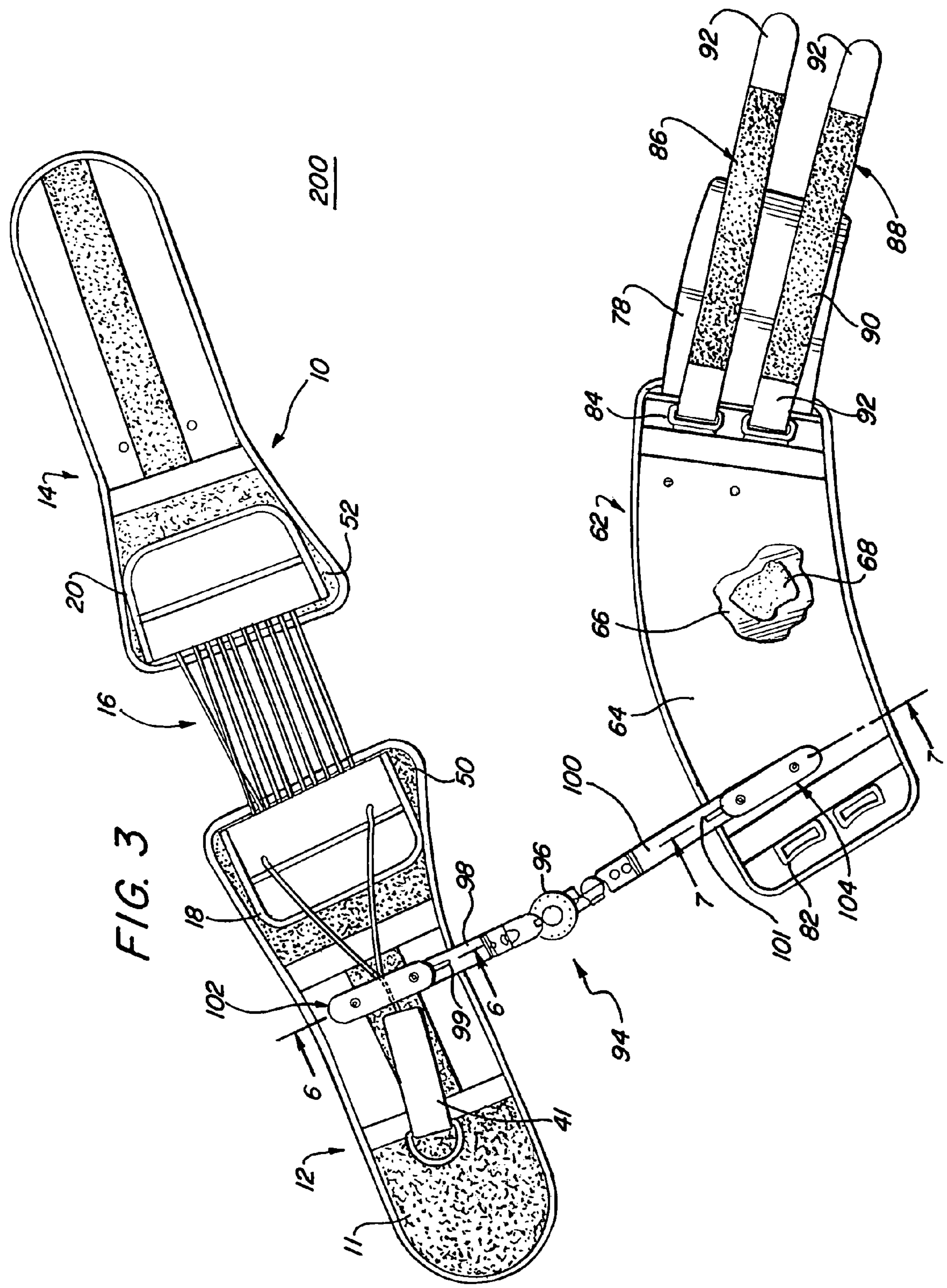
FIG. 3 is a plan view of the exterior of the hip orthosis.

The hip orthosis 200 includes a pelvic waist-engaging unit 10 as shown in FIGS. 1, 2 and 3. The waist-engaging unit 10 includes a first pelvic support member 12 and a second pelvic support member 14 that are interconnected by a closure unit 16.

The pelvic waist-engaging unit 10 is connected to a semi-rigid thigh supporting member 62 by a hinge unit 94. The hinge unit 94 can limit flexion, extension, adduction and abduction but only if it has a relatively rigid connection to both the user's waist and thigh. The present invention provides component parts for the pelvic waist-engaging unit that can be easily bent or flexed for mounting on the patient with a closure unit 16 that can provide a compressive force multiplication that enables the particular design of the pelvic support members 12 and 16 to become relatively rigid and thereby provide a stable anchor location for attachment of one end of the hinge unit 94. Likewise, the semi-rigid thigh supporting member 62 is designed to be flexible during mounting but also becomes relatively rigid to also provide a stable anchor location for the end of the hinge unit 94. The design of these component parts also enables a universal application to either a right or left thigh of a user.

Figure 9:
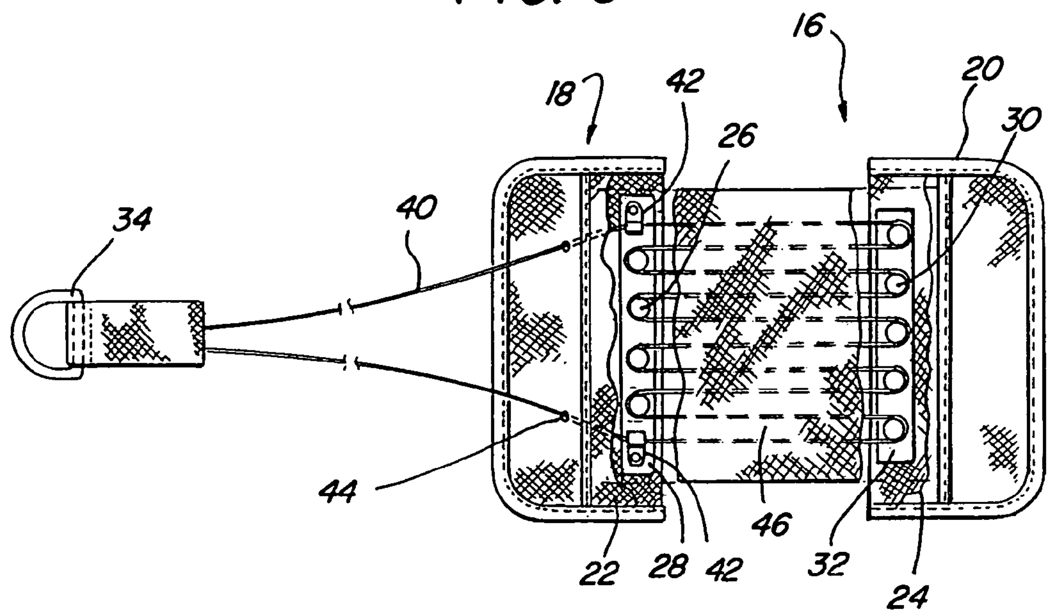
FIG. 9 is a front elevational view of the closure unit.
Figure 10:
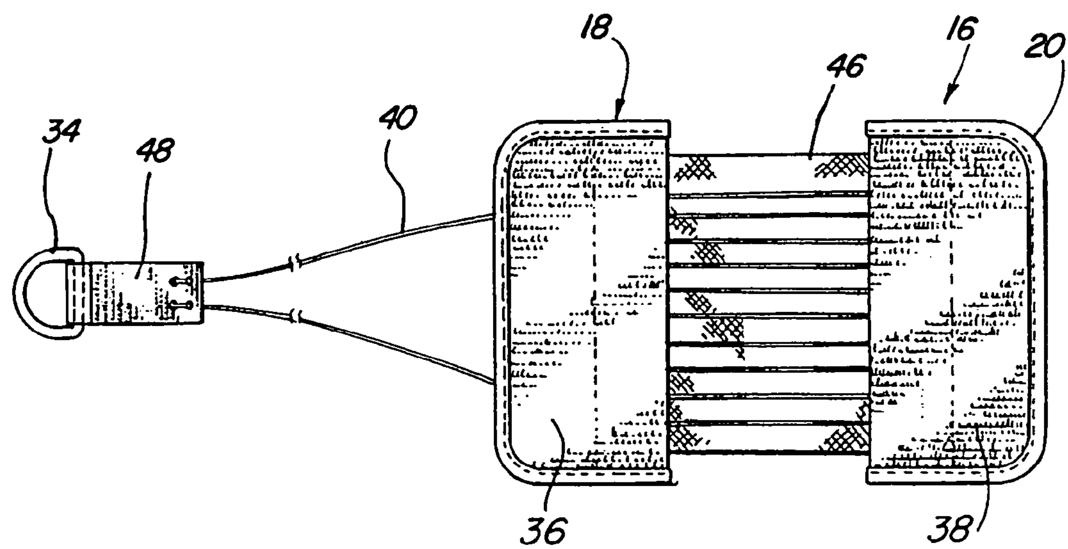
FIG. 10 is a rear elevational view of the closure unit.

Referring to FIGS. 9 and 10, the closure unit 16 includes a first closure member 18 and a second closure member 20 that include fastener portions on the underside, such as hook material 36 on the first connector member 18 and hook material 38 on a second connector member 20. The upper surface of these respective connector members can be divided into pockets 22 and 24 for covering and housing a plurality of support posts 26. The support posts 26 can be respectively affixed to a base member 28 on the first connector member 18 and support posts 30 are affixed to a base member 32 on the second connector member 20. The respective support posts extend upward from their respective base members and when mounted on a user or patient, will extend radially outward relative to a vertical axis about which the pelvic or waist-engaging unit 10 will encircle.

Each of the pockets 22 and 24 include an open slit to permit a cord member 40 to wrap around the respective support post 30 in a sliding operative mode of engagement to thereby permit a mechanical advantage or force multiplier when the cord member 40 is pulled by the user or patient. Cord member 40, preferably is an endless loop to permit force multiplication from each end of the loop and thereby limit the extent of force movement or displacement of the endless loop by the patient. A D ring 34, which can be grasped by the user, is attached to one end of the endless cord member 40. As seen on first connector member 18, the cords can pass through eyelets 42 and through an appropriate aperture 44 in the first connector member 18.

An elastic band 46 can be optionally provided to provide protection to the looped cord material to prevent interference or snagging on exterior projects. The elastic band 46 can stretch to accommodate relative movement between the first and second connector members 18 and 20 when a force is exerted by tightening the elongated cord member 40. The cord member 40 can be formed from a nylon material having an exterior braided surface to provide a low friction but strong pull member such as a Dacron cord with a diameter of 0.042 inches and a 90 pound test strength. One side of the attachment between the D ring 34 and the cord member 40 includes a strip of hook material 48. This hook material can interact with nap material position on an exterior of either the first pelvic support member 12 or the second pelvic support member 14 to provide an anchor position for locking the cord member 40 to the desired compressive force on the user.

Referring to FIG. 2, the first connector member 18 is shown mounted at a distal end of the first pelvic support member 12 while the second connector member 20 is shown mounted to the distal end of the second pelvic support member 14. While the first and second connector members can be permanently adhered to a pelvic support member, it is advantageous to utilize a nap and hook material such as Velcro™ material to thereby permit an adjustable alignment of the individual connector members of the closure unit. This permits a subjective adjustment to the particular anatomical features of the user or patient.

As seen also in FIG. 3, nap material 50 is provided on the distal end of the first pelvic support member 12 while nap material 52 is also provided on the distal end of the second pelvic support member 14. As also can be appreciated, the distal ends are enlarged to provide additional support to the lumbar section of the user. The front ends of the respective pelvic support members are removably attachable to each other. Pelvic support member 12 has an exterior front end of nap material 11 while pelvic support member 14 has a strip of nap material 15 on its exterior. The underside of the front end of pelvic support member 14 has hook material (not shown) for releasable engagement with the nap material on pelvic support member 12. A pull tab 41 has hook material and a D ring 34 whereby the user can tighten the closure unit 16 to the desired compressive force and maintain the force by attaching the pull tab 41 to the strip of nap material 15 as shown in FIG. 1.

Figure 8:
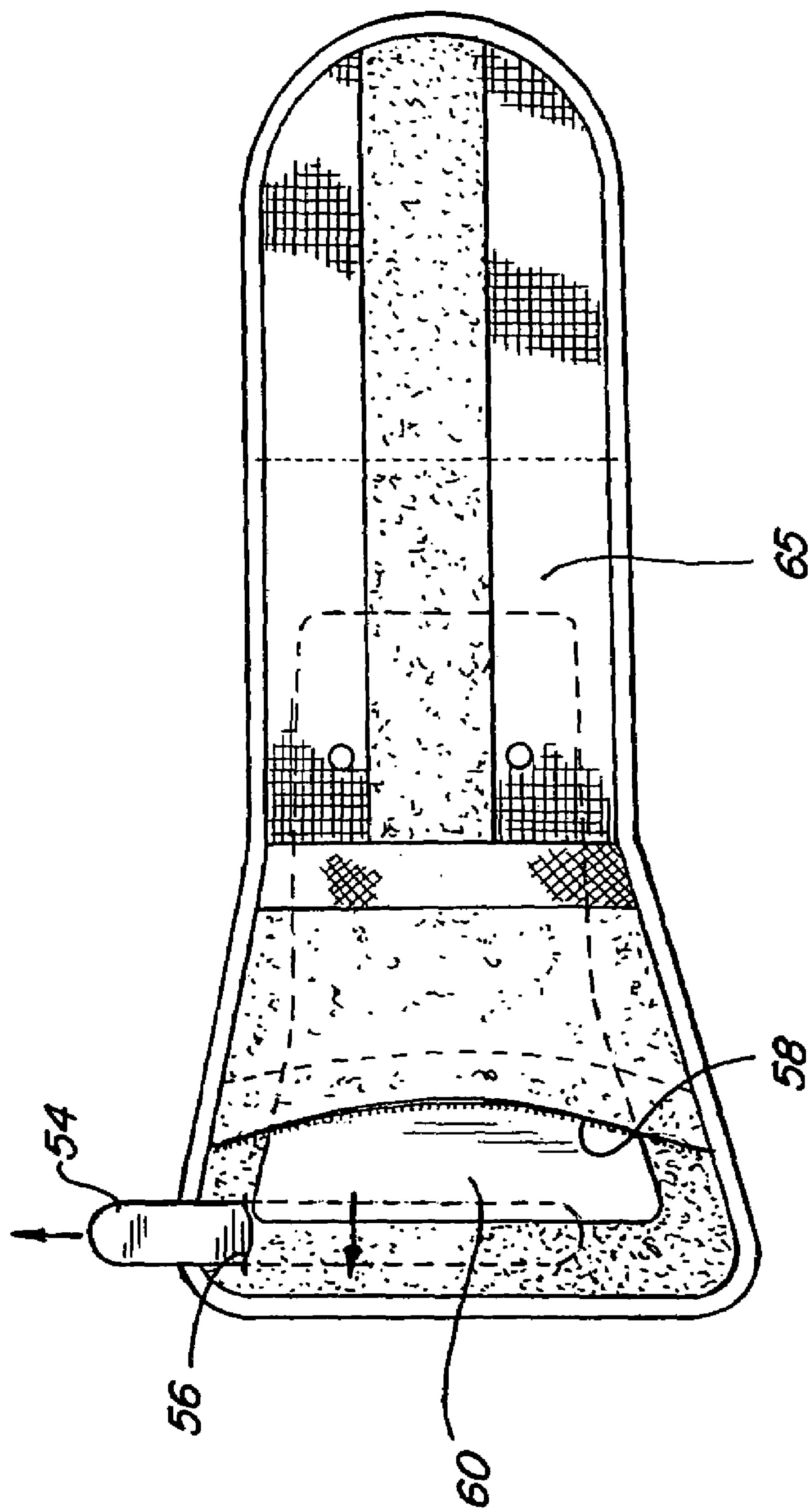
FIG. 8 is a perspective view of a pelvic support member with inserts.

As shown in FIG. 8, a stay 54 can be mounted within a pocket 56 at the respective distal ends of both the first pelvic support member 12 and the second pelvic support member 14 to provide additional stiffness in anchoring the respective first connector member 18 and the second connector member 20. Alternatively, the stays can be mounted on the exterior of the respective connector members without requiring a pocket. The stay 54 can be formed of an aluminum material for bendability to conform to the user's body or can be a plastic stay. A relatively air-porous hollow fabric covering member 65 encompasses each semi-rigid pelvic support member 12 and 14.

Another pocket 58 is provided adjacent the distal end and can receive a semi-rigid panel 60 for example, a plastic panel of an approximately trapezoidal shape, can be mounted within pocket 58. Thus, the central portion of the respective pelvic support members have a panel 60 of sufficient flexibility to bend and flex about a vertical axis of the user's waist, for conforming to the user's body while at the same time providing a higher resistance to bending about a traverse axis. The bending stiffness of the panel when mounted about the user is proportional to the moment of inertia in calculating stress and strain. In essence, with a circumferential wrap or bend of 130 degrees of the panel about the vertical axis of the user, it would be theoretically significantly stiffer than a panel with only a circumferential wrap of about 20 degrees. Basically, the issue is placing a trapezoidal shaped panel 60 into a somewhat semi-circular cylindrical configuration to prevent any rotation of the exterior of the panel about an axis lying in a horizontal plane traverse to the vertical axis.

To appreciate the relative dimensions of the each of pelvic support member 12 and 14, a medium size orthosis will be 19.5 inches in length with an enlarged distal end of 8.63 inches and an attaching end of 5.93 inches. The insert stay 60 can be a 0.06 inch thick of a high density polyethylene material with a length of 8.25 inches and an enlarged end width of 5.58 inches with a small end width of 4.48 inches. The anchor position for receiving a wedge support number 102 on the insert stay 60 can be 3.93 inches from the end of the enlarged end.

These dimensions enable an insert stay 60 to flex and bend in a central portion of the respective pelvic support member about a waist in such a manner to provide a sufficiently rigid anchor to stabilize movement of the leg in a controlled manner.

Figure 11:
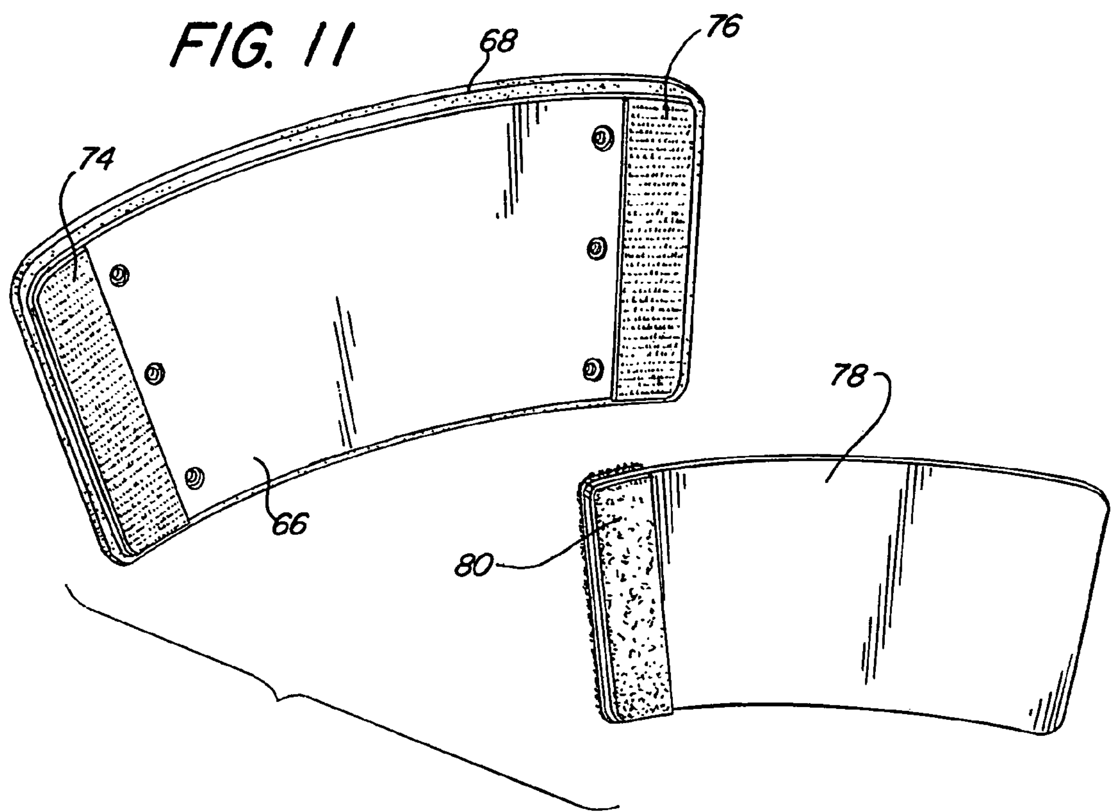
FIG. 11 is a front perspective view of a thigh support insert and extension.
Figure 12:
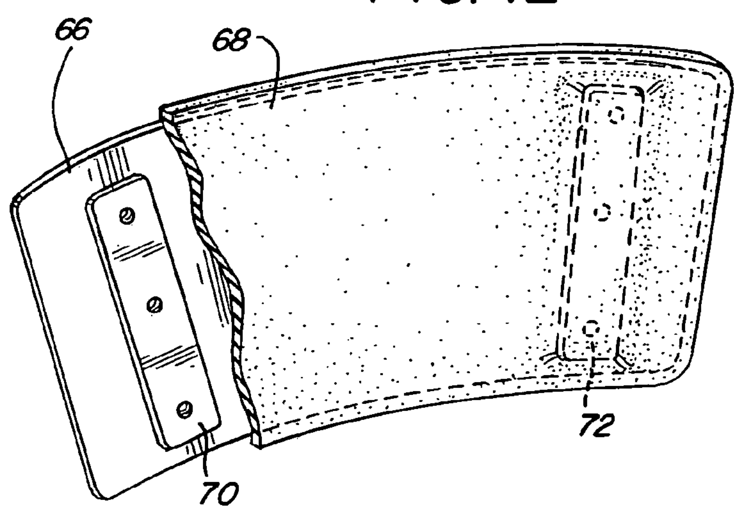
FIG. 12 is a rear perspective view of the thigh support insert.

A semi-rigid thigh support member 62, shown in FIG. 3, provides an arcuate exterior covering 64 that supports a plastic arcuate flexible sheet 66 that can be further optionally covered with a compressible foam layer 68. On one side of the plastic sheet 66 are aluminum rectangular anchor plates 70 and 72. As shown, three holes can be provided to receive fasteners for attachments to extension members of the hinge unit in each anchor plate. Thigh support member 62 is universal in that can be mounted on either the right or left leg of the user. Compressible foam layer 68 is mounted over the anchor plates 70 and 72 and can be adhered directly on one side of the plastic sheet 66. The other side of the plastic sheet 66, shown in FIG. 11, can have a strip of one of hook and nap material such as the hook material shown as strips 74 and 76. The exterior covering 64 actually is of a sleeve configuration and open at either end so that an extension tongue 78 also of a rectangular arcuate shape and having nap material 80 on both sides of the tongue can be connected to either hook material 74 or 76. As can be appreciated, different size extension tongues can be used or a cutting of the extension tongue can be performed to customize the size of the thigh support member 62 to the thigh of the individual patient.

Referring to FIG. 3, a pair of plastic anchor slot members 82 can be provided on one side of the thigh support member 62, and a corresponding pair of slotted anchor members 84 can be provided on the other side of the thigh support member 62. A pair of straps 86 and 88 have a central portion of a nap material 90 on both sides, with a pair of tongues 92 at the respective ends. The tongues have on one side a hook material. The straps 86 and 88 can be appropriately attached to one set of slotted anchor members by the lapping of the hook member back over the central nap material and the other end of the hook material can then be inserted through the slotted anchor member 82 as shown in FIG. 3, tightened, and then the hook material 92 can be appropriately fastened to the central nap material to provide an attachment of the semi-rigid thigh support member 62 about the thigh of the user as shown in FIG. 1. As a result of this design, a universal thigh support member is provided thereby avoiding a requirement of providing separate right and left thigh members and an unnecessary duplication of inventory.

Figure 6:
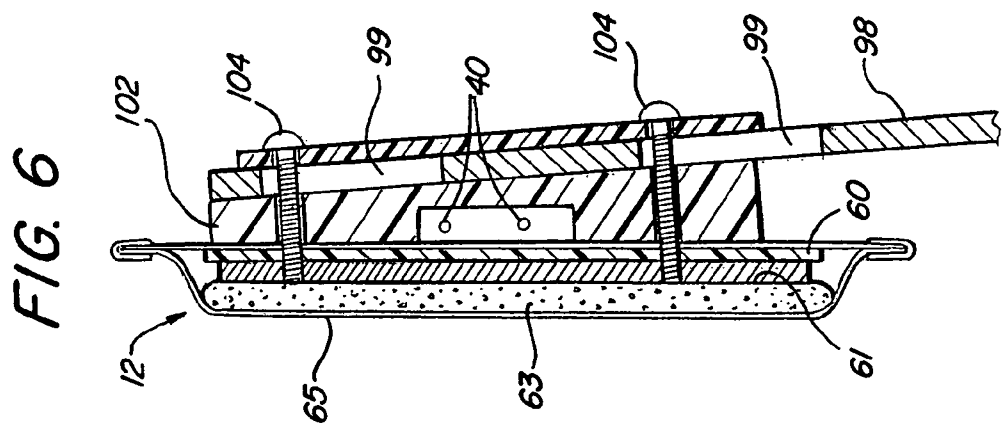
FIG. 6 is a partial cross-section of the pelvic support member shown in FIG. 3.

A hinge unit 94 includes a hinge member 96 that can be used to adjust abduction and adduction. As can be appreciated, there are a number of different hinge units that can be commercially available, including the hinges shown in U.S. Pat. No. 6,589,195. The hinge member 96 is connected to an upper extension member 98 and a lower extension member 100. The slotted apertures 99, 101 in the respective upper and lower extension members, permit an adjustable connection to anchor points respectively in the pelvic engaging unit 10 and the thigh support member 62. Wedge support member 102 can be connected as shown in FIG. 6 to one of the semi-rigid pelvic support members.

As shown in FIG. 3, the first pelvic support member 12 has the upper extension member 98 connected through screw fasteners 104 to an anchor member such as an oblong anchor plate 61. A compressible foam layer 63 covers both the anchor plate 61 and the trapezoidal shaped panel 60. A breathable outer covering 65 surrounds the trapezoidal shaped panel 60. The wedge support member 102 increases in thickness in a direction towards the hinge member 96. This enables the hinge member 96 to be adequately displaced from the hip and leg of the user. The slotted holes 99 permit adjustment of the relative distance between the waist engaging unit 10 and the thigh support member 62.

Figure 7:
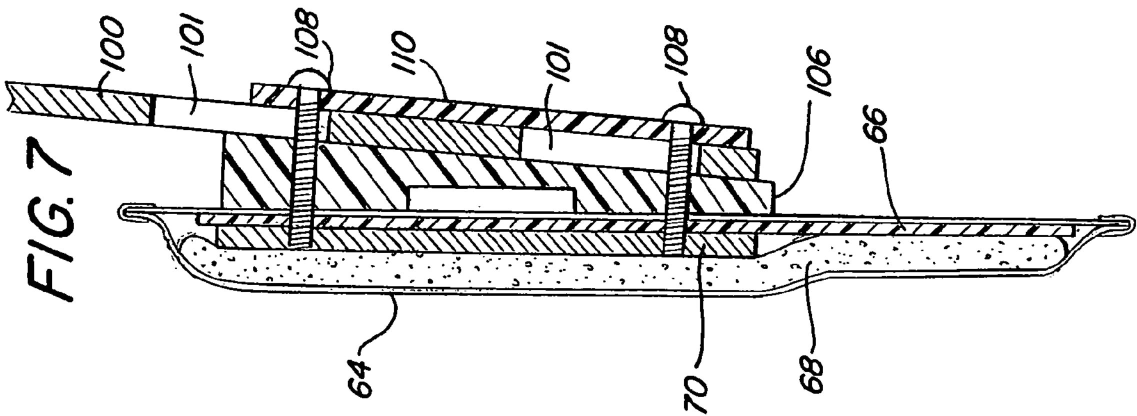
FIG. 7 is a partial cross-section of the thigh support member shown in FIG. 3.

FIG. 7 shows a cross-sectional view of a connection of the lower extension member 100 with slotted apertures 101 and fasteners 108 connected to the anchor plate 70 after the fasteners 108 pass through the waist support member 106. The thickness of the wedge support member 106 is progressively larger towards the hinge member 96. Plastic caps 110 can be optionally used with the respective fasteners 104 and 108 to capture the respective extension members 98 and 100.

Figure 5:
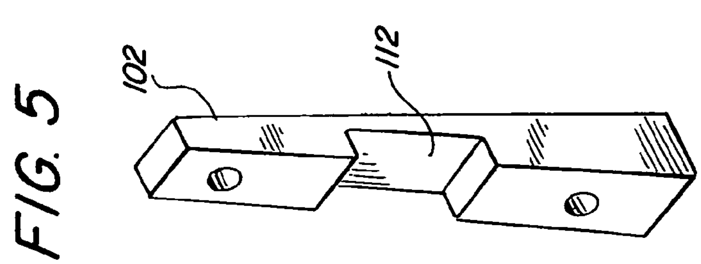
FIG. 5 is a perspective of a wedge support member.

As can be seen in FIG. 5, the wedge members 102, 106 include a central aperture or passageway 112 to capture and permit clearance for the cord member 40.

Figure 13:
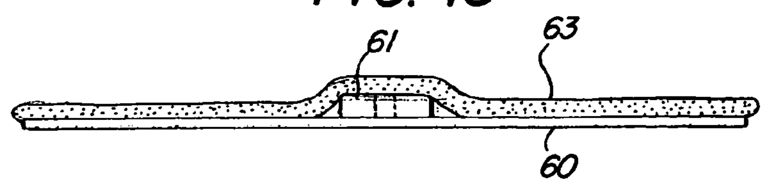
FIG. 13 is a top view of the pelvic support insert.

Referring to FIG. 13, a side view of the trapezoidal shaped panel 60 that is inserted within the pocket 58 of the respective pelvic support members 12 and 14 can be seen.

Figure 4:
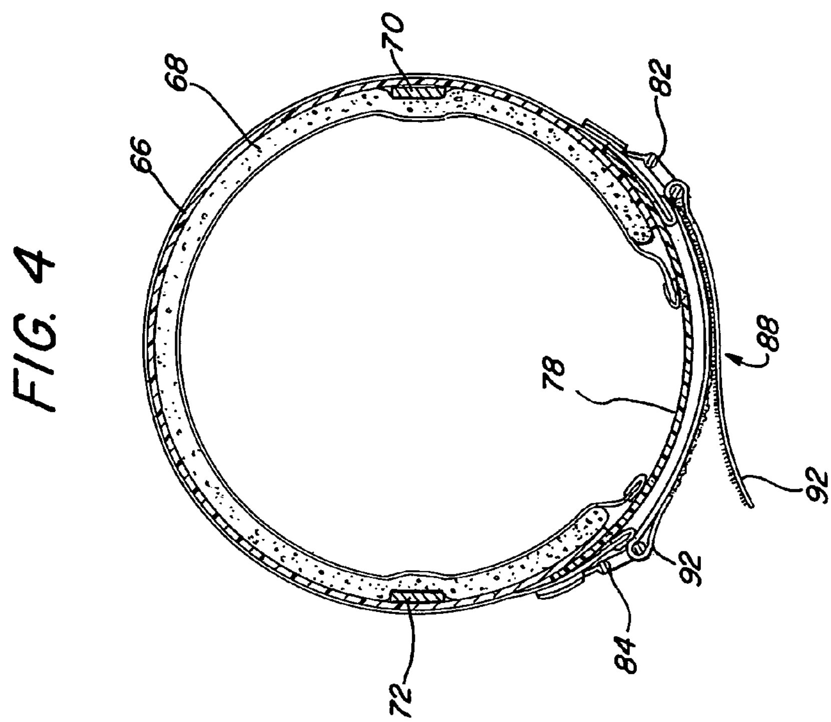
FIG. 4 is a cross-sectional view of the thigh support member shown in FIG. 1.

Referring to FIG. 4, a cross-sectional view of the thigh member support 62 in a closed configuration is shown. The anchor plates 70 and 72 are layered between the compressible foam layer 68 and the plastic arcuate sheet 66. By providing the pair of anchor plates 70 and 72, a universal thigh member can be achieved for either the right or left leg. The extension tongue 78 is also reversible because of the removable hook and nap connection and further, can be either cut down to the appropriate size for the patient or an alternative tongue can be included. Additionally, the straps 86 and 88 can also be adjusted for fastening to either the slotted anchor members 82 or 84.

As can be readily appreciated, a versatile lightweight orthoses can be provided with the combination of the waist engaging unit 10 and the thigh support member 62. The present design takes advantage of the stiffening ability of bending thin sheets of plastic of the waist or pelvic support members and the thigh support member on the user to provide a rigidity that is generally achieved only with a hard shell plastic configuration.

By providing an easily donnable and lightweight configuration, the prophylactic treatment advantages of the orthosis can be achieved while encouraging prolonged use by the patient. The design of the individual modular components increases the economy that can be achieved with the present invention.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A hip orthosis comprising:

a pair of semi-rigid pelvic support members removably attachable to each other at one end;

a closure unit, attached to respective distal ends at each one of the pair of pelvic support members to provide a mechanical force advantage in compressing the pelvic support members on a patient wherein a force exerted by a user is multiplied, wherein the closure unit is removably connected to the pair of pelvic support members and includes a first closure member with a first plurality of support posts and a second closure member with a second plurality of support posts, and a flexible elongated member operatively extending around and between the first and second plurality of support posts to provide the mechanical force advantage, the flexible elongated member is a low friction cord that enables a sliding movement of the cord around the first and second plurality of support posts;

a semi-rigid thigh support member for removable mounting on the thigh of a user, having a pair of spaced anchor plates;

a hinge unit having an upper extension member for attachment to one of the pelvic support members, a lower extension member for attachment to the thigh support member and a hinge member connected to the respective upper extension member and lower extension member to enable relative movement;

a first wedge support member; and a second wedge support member, the first wedge support member is removably attached to one of the pelvic support members and the second wedge support member is removably attached to the thigh support member through one of the pair of anchor plates, the first and second wedge support members are configured to be adjustably attached respectively to the upper extension member and the lower extension member to accommodate a length and abduction adjustments for a user, wherein each of the pair of semi-rigid pelvic support members include a fabric covering member encompassing a semi-rigid waist elongated panel, one of the elongated panels are affixed to the first wedge support member at a location that enables a universal use for either a right or left side of a user.

2. The hip orthosis of claim 1, wherein the flexible elongated member is an endless cord and the first and second plurality of support members are posts that enable a sliding movement of the endless cord.

3. The hip orthosis of claim 1, wherein the first wedge support member has a passageway to accommodate and locate a portion of the cord.

4. The hip orthosis of claim 1, wherein each of the pair of pelvic support members have a larger height at a distal end relative to the attachment end, to permit adjustable location of the compound closure unit and to provide lumbar support for the user.

5. The hip orthosis of claim 1, wherein the thigh support member has a pair of slotted anchor or members and a pair of reversible straps, only one strap passes through a respective slot for securement of the strap on a user and can enable universal use of the thigh support member for either the right or left side of the user.

6. The hip orthosis of claim 5, wherein the thigh support member includes a hollow fabric covering member and a semi-rigid thigh elongated plastic panel of an arcuate truncated configuration tightly inserted in to the hollow fabric covering member with the pair of anchor plates attached to the semi-rigid thigh elongated panel.

7. The hip orthoses of claim 1 wherein the semi-rigid thigh support member further includes a reversible extension tongue member that is removably-mounted to either end of the semi-rigid thigh support member to accommodate mounting on respectively the right or left thigh of the user.

8. The hip orthosis of claim 1 wherein each of the semi-rigid waist elongated panels have an approximately trapezoid shape.

9. The hip orthosis of claim 1 wherein the anchor plates are oblong with a plurality of threaded holes.

10. The hip orthosis of claim 1 wherein an elongated stay can be mounted in each of the first and second semi-rigid pelvic support members to provide support for the closure unit.

11. The hip orthosis of claim 1 wherein each of semi-rigid pelvic support members are flexible at first ends with nap and hook material for removable attachment, have a semi-rigid central portion, have an intermediate flexible portion and are semi-rigid towards second ends that support the closure unit.

* * * * *